United States Patent
Salier et al.

(10) Patent No.: US 7,985,549 B2
(45) Date of Patent: Jul. 26, 2011

(54) METHOD FOR PREDICTING RESPONSIVENESS TO TNFα BLOCKING AGENTS

(75) Inventors: Jean-Philippe Salier, Les Authieux-Ratieville (FR); Maryvonne Daveau, Mont-Saint-Aignan (FR); Anne-Christine Gauthier-Jauneau, Pont de l'Arche (FR); Olivier Vittecoq, Saint Ouen de Thouberville (FR); Xavier Le Loet, Rouen (FR); Alain Daragon, Rouen (FR); Othmane Mejjad, Houppeville (FR); Thierry Lequerre, MontMain (FR)

(73) Assignee: INSERM (Institut National de la Sante et de la Recherche Medicale), Paris cedex (FR)

( * ) Notice: Subject to any disclaimer, the term of this patent is extended or adjusted under 35 U.S.C. 154(b) by 226 days.

(21) Appl. No.: 12/300,847

(22) PCT Filed: May 15, 2007

(86) PCT No.: PCT/IB2007/002373
§ 371 (c)(1),
(2), (4) Date: Nov. 14, 2008

(87) PCT Pub. No.: WO2007/135568
PCT Pub. Date: Nov. 29, 2007

(65) Prior Publication Data
US 2009/0252740 A1  Oct. 8, 2009

(30) Foreign Application Priority Data
May 16, 2006 (EP) .................................. 06290789

(51) Int. Cl.
*C12Q 1/68* (2006.01)
*G01N 33/53* (2006.01)
*C12N 15/11* (2006.01)
*C12N 15/12* (2006.01)
*C07H 21/04* (2006.01)

(52) U.S. Cl. .......... 435/6; 435/7.1; 536/23.5; 536/24.31

(58) Field of Classification Search .................. None
See application file for complete search history.

(56) References Cited

U.S. PATENT DOCUMENTS
2005/0196799 A1  9/2005  Wigler et al.

OTHER PUBLICATIONS

R. Maini et al., "Infliximab (chimeric anti-tumour necrosis factor alpha monoclonal antibody) versus placebo in rheumatoid arthritis patients receiving concomitant methotrexate: a randomized phase III trial", The Lancet Limited, London, GB, vol. 354, No. 9194, Dec. 4, 1999, pp. 1932-1939.

T. Lequerre et al., "Gene expression profiling in PBMCs as a tool for prediction of infliximab responsiveness in rheumatoid arthritis", Arthritis & Rheumatism, vol. 50, 2004, p. S398.

T. Lequerre et al., "Prediction of infliximab responsiveness in rheumatoid arthritis from gene profiling in PBMCs, but not with autoantibodies (autoab), metalloproteinases and bone markers parameters in sera of patients", Arthritis & Rheumatism, vol. 52, No. 9S, Sep. 2005, pp. S569-S570.

*Primary Examiner* — James Martinell
(74) *Attorney, Agent, or Firm* — Occhiuti Rohlicek & Tsao LLP (57) ABSTRACT

The invention provides an in vitro method for predicting whether a patient would be responsive to a treatment with a TNFα blocking agent, which method comprises determining the expression level of eight genes in a biological sample of said patient, wherein said genes are EPS15, HLA-DPB1, AKAP9, RASGRP3, MTCBP-1, PTNP12, MRPL22 and RPS28. The invention further provides a DNA chip for performing such method.

21 Claims, 1 Drawing Sheet

FIG. 1

METHOD FOR PREDICTING RESPONSIVENESS TO TNFα BLOCKING AGENTS

CROSS REFERENCE TO RELATED APPLICATIONS

This application is the national phase of International Application No. PCT/IB2007/002373 filed May 15, 2007 which claims priority to European application number 06290789.4 filed May 16, 2006. The contents of which are hereby incorporated by reference in their entirety.

The present invention relates to a method for predicting the response to a treatment with a TNFα blocking agent.

Rheumatoid arthritis (RA) is a chronic, auto-immune and inflammatory polyarthritis which induces joint damage and disability. Tumor Necrosis Factor-α (TNFα) plays a key role in the associated pathologic events and has been identified as a therapeutic target. In fact, TNFα blocking agents (TBA) such as infliximab, etanercept, and adalimumab have revolutionized the therapeutic caring of methotrexate-resistant patients. Various clinical trials with a TBA/methotrexate combination have shown efficacy in 60-80% of such patients. TBAs reduce joint inflammation, slow down joint damage and improve physical function. Still, 20-40% of the RA patients given a TBA/methotrexate combination do not respond to this treatment. Moreover, TBAs may have side effects and are costly and the efficacy of any given TBA in a given patient is unpredictable. For these reasons, predicting responsiveness to a given TBA would be most useful.

Because genetic polymorphisms such as HLA-DR haplotypes have been associated with a variable natural course of RA and a heterogeneous response to conventional disease-modifying anti-rheumatic drugs (DMARD), a few studies have attempted to identify genetic markers for TBA efficacy and they have focused on the promoters of several cytokine genes (Kang C P et al. 2006; Mugnier et al. 2003; Cuchacovich et al. 2004). For example, sequence variation in the TNFα gene promoter has been associated with a variable response to infliximab (Mugnier et al. 2003). However, similar conclusions hold true for etanercept as well (Mugnier et al. 2004) and hence such genotypings are useless for selecting the TBA with greatest benefits (Lequerré T et al. 2005). Because response to treatment likely depends on polymorphisms at multiple loci (Briges S L et al. 2004), genomewide analysis of gene expression with cDNA arrays has been recently used to identify markers of responsiveness in the peripheral blood mononuclear cells (PBMCs). However, the number of such studies is still very limited (Kekow et al. 2004; Meisel et al. 2004) and very few informative genes have been identified (Kekow et al. 2004). Moreover, in all instances too few patients per study precluded statistically valid conclusions (Meisel et al. 2004) or a confirmatory analysis in another, independent set of patients (Kekow et al. 2004).

The preliminary search of predictive parameters was disclosed by the inventors in various conferences (American College of Rheumatology 2005, San Diego, 13-17 Nov. 2005; American College of Rheumatology 2004, San Antonio, 19-21 Oct. 2004; Journée scientifique du Club Rhumatisme et Inflammation (CRI) Jun. 4, 2004, Paris (Institut Pasteur), Journée de l'IFRMP 2004, Jun. 18, 2004, Dieppe.; Congrès national de la Société Française de Rhumatologie (SFR) 2005, Dec. 4-7, 2005, CNIT de la Défense, Paris; Congrès national de la Société Française de Rhumatologie (SFR) 2004, Nov. 15-17, 2004, CNIT de la Défense, Paris).

SUMMARY OF THE INVENTION

Owing to transcriptome analysis in PBMCs from RA patients, the inventors have now identified a small subset of transcripts whose combined levels allow one to reliably predict the response to treatment with a TNFα blocking agent.

On this basis the invention provides an in vitro method for predicting whether a patient would be responsive to a treatment with a TNFα blocking agent, which method comprises determining the expression level of eight genes in a biological sample of said patient, wherein said genes are EPS15, HLA-DPB1, AKAP9, RASGRP3, MTCBP-1, PTNP12, MRPL22 and RPS28.

The combined expression profile of these genes is informative of the status of the patient who, before any treatment with a TNFα blocking agent, can be classified as responder or non-responder, and be given the appropriate treatment.

The method usually comprises the further step of comparing the expression level of said genes with reference values obtained from responder and non-responder groups of patients. The patient is preferably with rheumatoid arthritis, most preferably, wherein the patient is with rheumatoid arthritis that is active.

In a preferred embodiment, TNFα blocking agent is an anti-TNFα antibody, e.g. infliximab.

The patient to be tested may receive a basic treatment other than TNFα blocking agent, e.g. he/she may be treated with methotrexate, azathioprine or leflunomide.

The expression level is advantageously determined by quantifying the level of mRNA of said genes in the biological sample. Using a DNA chip is particularly useful in that respect. The assay using such a chip is indeed reliable, fast, and cheap.

A further subject of the invention is the DNA chip that allows to perform such method, i.e. a DNA chip comprising a solid support which carries nucleic acids that are specific to EPS15, HLA-DPB1, AKAP9, RASGRP3, MTCBP-1, PTNP12, MRPL22 and RPS28 transcripts.

DETAILED DESCRIPTION OF THE INVENTION

The method of the invention is based on the identification of a set of genes whose combined expression profiles allow to distinguish patients between responder and non-responder to a treatment with a TNFα blocking agent.

In practice, the rapid determination of the expression level of said genes, e.g. by a quantitative RT-PCR, offers a powerful tool for predicting responsiveness to a TNFα blocking agent.

The study presented in the Example shows that such analysis allows to predict efficacy of TNFα blocking agents, such as infliximab, with a sensitivity of 80%, a specificity of 100%, and a positive predictive value of 100%, and a negative predictive value of 83%.

DEFINITIONS

The term "patient" refers to any subject (preferably human) afflicted with a disease likely to benefit from a treatment with a TNFα blocking agent, in particular a TNFα-related disease.

The TNFα-related diseases encompass an autoimmune disorder, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, and vasculitis. In one embodiment, the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephrotic syndrome. In another embodiment, the TNFα-related disease is selected from the group consisting of inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity, and radiation toxicity. In still another embodiment, the TNFα-related disease is selected from the group consisting of Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In one embodiment of the invention, the TNFα related disease is Crohn's disease. In another embodiment, the disease is ulcerative colitis. In still another embodiment, the disease is psoriasis. In still another embodiment, the disease is psoriasis in combination with psoriatic arthritis (PsA).

In the preferred embodiment, the TNFα-related disease is rheumatoid arthritis.

The method of the invention is particularly useful to predict the response to a treatment by a TNFα blocking agent in a patient with rheumatoid arthritis that is active. The disease activity can be measured according to the standards recognized in the art. The "Disease Activity Score" (DAS) is a measure of the activity of rheumatoid arthritis. In Europe the DAS is the recognized standard in research and clinical practice.

The following parameters are included in the calculation (Van Gestel et al, 1996):
    Number of joints tender to the touch (TEN)
    Number of swollen joints (SW)
    Erythrocyte sedimentation rate (ESR)
    Patient assessment of disease activity (VAS; mm)
    Patients with a disease activity score 28 (DAS28)≧5.1 are a preferred group of patients.

Patients who are resistant to methotrexate (MTX), usually considered first-line therapy for the treatment of RA, are a further preferred group of patients for whom the method of the invention can be particularly useful.

More generally, patients who already receive a basic treatment for their TNFα-related disease, e.g. with MTX, azathioprine or leflunomide, are particularly good candidates for the test method of the invention.

After being tested for responsiveness to a treatment with TNFα blocking agent, the patients may be prescribed with a TNFα blocking agent with or without the same basic treatment. In particular the combination infliximab/MTX can be particularly effective in patients with RA and other TNFα-related disease.

The term "biological sample" means any biological sample derived from a patient, preferably a sample which contains nucleic acids. Examples of such samples include fluids, tissues, cell samples, organs, biopsies, etc. Most preferred samples are blood, plasma, saliva, urine, seminal fluid, etc. Peripheral blood is preferred, and mononuclear cells (PBMCs) are the preferred cells. Total RNAs can be easily extracted therefrom. The biological sample may be treated prior to its use, e.g. in order to render nucleic acids available. Techniques of cell or protein lysis, concentration or dilution of nucleic acids, are known by the skilled person.

"TNFα blocking agent" refer to molecules, such as proteins or small molecules, that can significantly reduce TNFα properties. TNFα, a naturally occurring cytokine, plays a central role in the inflammatory response and in immune injury. It is formed by the cleavage of a precursor transmembrane protein, forming soluble molecules which aggregate to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Such blocking agents include anti-TNFα antibodies, e.g. infliximab, adalimumab, CDP571 or D2E7. Recombinant TNF-receptor based proteins have also been developed (e.g. etanercept, a recombinant fusion protein consisting of two soluble TNFα receptors joined by the Fc fragment of a human IgG1 molecule). A pegylated soluble TNF type 1 receptor can also be used as a TNF blocking agent. Additionally, thalidomide has been demonstrated to be a potent anti-TNF agent. TNFα blocking agents thus further include phosphodiesterase 4 (IV) inhibitor thalidomide analogues and other phosphodiesterase IV inhibitors.

A "responder" patient, or group of patients, refers to a patient, or group of patients, who shows or will show a clinically significant relief in the disease when treated with a TNFα blocking agent. When the disease is RA, a preferred responder group of patients that provides for the control values is a group that shows a change of DAS28 ≧1.2 after three months of treatment with a TNFα blocking agent such as infliximab.

The expression level of the genes is determined and compared between a responder group and a non-responder group of patients. Said expression level of genes" correspond to the combined expression profile of said genes in either group.

Figure 1:
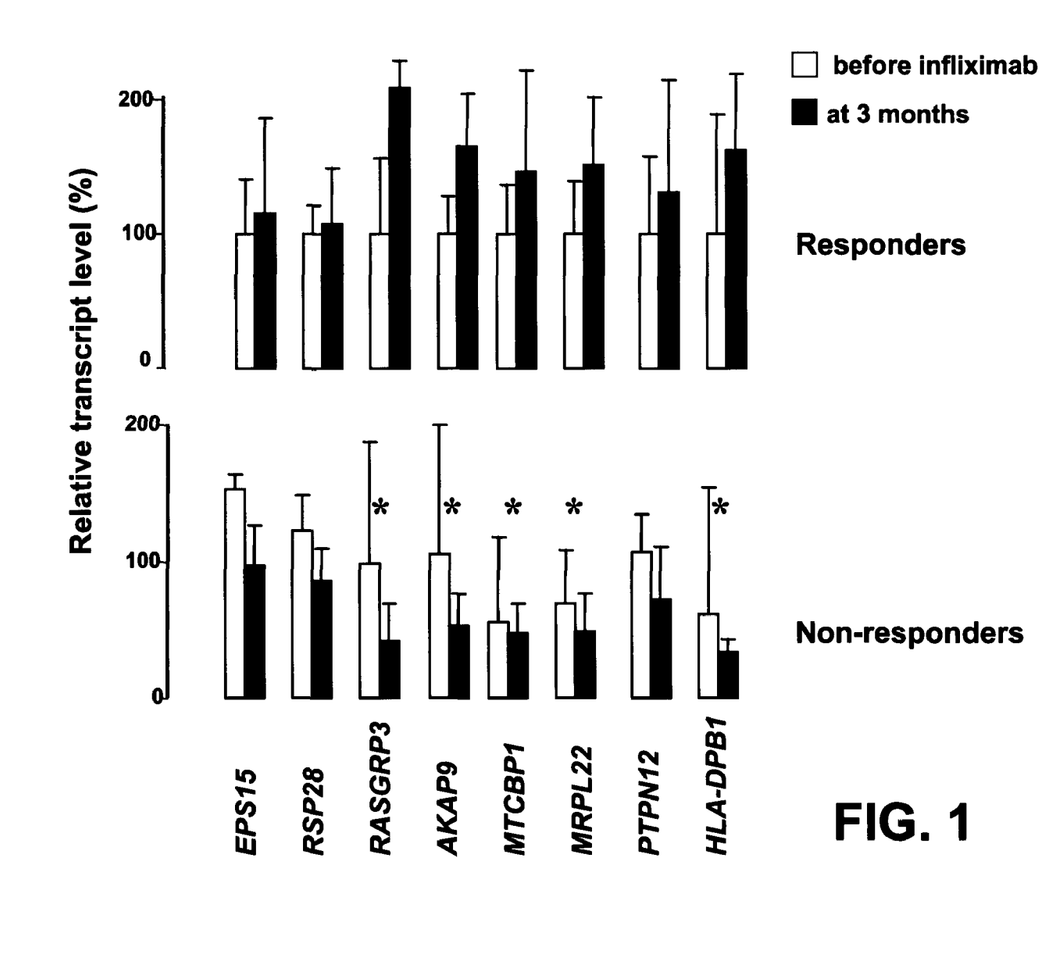
FIG. 1 shows the relative transcript levels at baseline vs 3 months in responders or non-responders. For every transcript, the 4 levels (median value) shown at baseline and after 3 months in responders and non-responders are expressed as a percentage of the median level at baseline in responders (100%). Significant differences are all noted in the non-responder panel: star outside closed bar, difference in non-responders at baseline vs 3 months (p<0·05, paired Wilcoxon's test); star within closed bar, difference at 3 months in responders vs non-responders (p<0·05, Mann and Whitney's test). In any patient group, a trend towards an increased or decreased level was so considered whenever the value at 3 months was respectively above or below the value at baseline, whatever the difference of these values.

Expression profiles in responder and non-responder groups are shown in FIG. 1.

The comparison between groups can be performed by computer tools, such as the supervised learning classification tool Support Vector Machine (SVM). These tools take into account the differential expression of the gene clusters, i.e. of the combination of the genes between groups, and generate an algorithm. The latter next allows for a prediction of the non-responder or responder status of any further patient, provided the same transcript level have been determined in said patient.

The Sets of Predictive Genes

All the genes identified are known per se, and listed in the below tables A and B. Table A presents the set of eight genes whose combined expression profile has been shown to be informative with regard to responsiveness to a treatment with TNFα blocking agent. These are EPS15, HLA-DPB1, AKAP9, RASGRP3, MTCBP-1, PTNP12, MRPL22 and RPS28 transcripts.

This being said, it is also contemplated to make use of only a subcombination of these transcripts, e.g. a subcombination of 4 or 5 of them.

TABLE A subset of 8 genes (transcripts)

| Gene | EMBL access number | Description | Seq ID NO: |
|---|---|---|---|
| EPS15 | BC051873 | epidermal growth factor receptor pathway substrate 15 | 1 |
| HLA-DPB1 | AY656678 | HLA-DP HISTOCOMPATI- BILITY TYPE, BETA-1 SUBUNIT | 3 |
| AKAP9 | BC015533 | A-kinase anchor proteins (AKAPs) | 5 |
| RASGRP3 | BC027849 | RAS guanyl releasing protein 3 (calcium and DAG-regulated) | 7 |
| MTCBP-1 | AB158319 | Membrane-type 1 matrix metalloproteinase cytoplasmic tail binding protein-1 (MTCBP-1) | 9 |
| PTNP12 or PTPN12 | BC050008 | protein tyrosine phosphatase, non-receptor type 12 | 11 |
| MRPL22 | BC012565 | mitochondrial ribosomal protein L22 | 13 |
| RPS28 | BC070218 | ribosomal protein S28 | 15 |

EPS15

This gene encodes a protein that is part of the EGFR pathway. The epidermal growth factor receptor pathway substrate 15 (EPS15) is present at clatherin-coated pits and is involved in receptor-mediated endocytosis of EGF. Alternate transcriptional splice variants of this gene have been observed.

HLA-DPB1

The HLA-DPB1 gene encodes the HLA-DP histocompatibility type, beta-1 subunit. HLA-DPB belongs to the HLA class II beta chain paralogues. This class II molecule is a heterodimer consisting of an alpha (DPA) and a beta chain (DPB), both anchored in the membrane. It plays a central role in the immune system by presenting peptides derived from extracellular proteins.

AKAP9

The AKAP9 gene encodes the A-kinase anchor proteins (AKAPs) which is a group of proteins which have the commun fonction of binding to the regulatory subunit of protein kinase A. Alternative splicing of this gene results in many isoforms which interact with different proteins involved in multiple signal transduction pathways. Those proteins include type II protein A, serine/threonine protein kinase N, protein phosphatase 1, protein phosphatase 2a.

RASGPR3

The RASGPR3 gene encodes the RAS guanyl releasing protein 3 (calcium and DAG-regulated) which belongs to the subfamily of GTPases. It plays a role in signal transduction. Guanine nucleotide exchange factors (GEFs), such as RAS-GRP3, serve as RAS activators by promoting acquisition of GTP to maintain the active GTP-bound state and are the key link between cell surface receptors and RAS activation.

MTCPB1

The MTCPB1 gene encodes the Membrane-type 1 matrix metalloproteinase cytoplasmic tail binding protein-1 (MTCBP-1) which binds the cytoplasmic tail of membrane-type 1 matrix metalloproteinase. This protein is weakly expressed in tumor cell lines. It plays a role in cell adhesion and inhibition of cell proliferation.

PTPNI2

The PTPN12 gene encodes the protein tyrosine phosphatase, non-receptor type 12 which is a member of the tyrosine phosphatase (PTP) family. PTP are known to be signalling molecules in a variety of cellular processes such as cell differentiation, mitotic cycle, and oncogene transformation.

MRPL22

Mammalian mitochondrial ribosomal proteins are encoded by nuclear genes and help in protein synthesis within the mitochondrion. Mitochondrial ribosomes (mitoribosomes) consist of a small 28S subunit and a large 39S subunit. Among different species, the proteins comprising the mitoribosome differ greatly in sequence, and sometimes in biochemical properties, which prevents easy recognition by sequence homology. This gene encodes a 39S subunit protein that belongs to the L22 ribosomal protein family.

RSP28

The RSP28 gene encodes the ribosomal protein S28 that is a component of the 40S subunit of ribosome. The protein belongs to the S28E family and is located in the cytoplasm.

In a particular embodiment, the method of the invention further comprises determining the expression level of the genes of Table B, or of a subcombination thereof (combined with the set of eight genes as defined in Table A):

TABLE B

Other transcripts of interest for the predictive method

| Transcript | EMBL access number | Seq ID |
|---|---|---|
| AADAT | BC031068 | 17 |
| COX7AL2 | NM_001865.2 | 19 |
| CXCL5 | BC008376 | 21 |
| ELMOD2 | BC015168 | 23 |
| FBXO5 | BC018905 | 25 |
| KNG1 | BC060039 | 27 |
| LAMR1 | BC070263 | 29 |
| MUCDHL | AY358368 | 31 |
| PFKFB4 | AF108765 | 33 |
| PSMB9 | BC065513 | 35 |
| RPL35 | BC000348 | 37 |
| RPS16 | M60854 | 39 |
| TBL2 | AF097484 | 41 |
| THRAP3 | BC112350 | 43 |
| 193472 Kininogen 1 | BC060039 | 45 |
| 239932 | ELAC homolog 2 | 47 |
| QIL-1 | NM 205767 | 49 |
| SCAM-1 | BC 016355 | 51 |
| MUSTN1 | AC D 38595 | 53 |
| WDR39 | NM025396,2 | 55 |
| 114519 | BC 011054 | 57 |
| 415079 | DKFZP566MP046 | 59 |
| 244313 | HS21640657 (EST) | 60 |
| 295669 | HS.562814 (EST) | 61 |
| 234261 | HS4622065 (EST) | 62 |
| 123983 | Hs.98510 | 63 |
| 82303 | HS4622065 (EST) | 64 |
| 247176 | HS573014(EST) | 65 |

The list of transcripts does not disclose any significant series of transcripts whose altered levels could point to the physiopathological importance of a predominating function or pathway. Indeed, these transcripts coversuch diverse proteins and functions as ribosomal components (LAMR1, MRPL22, RPL35, RPS16, RPS28), cell adhesion and inhibition of cell migration/invasion (LAMR1, MUCDHL, MTCPB1), cytochromes (CYP3A4, CYP4F12) and cytochrome oxidase (COX7A2L), proteasome-mediated proteolysis (FBXO5, PSMB9), various enzymes (MDAT, PFKFB4), intra- or extra-cellular signalling (AKAP9, CXCL5, PTPN12, RASGRP3, TBL2, THRAP3), this including regulators of the ERK pathway (EPS15, SCAM-1), and innate or adaptive immunity (KNG1, MCP, PSMB9, HLA-DPB1). However, two transcripts, namely MUSTN1 and HLA-DPB1, are noteworthy. Indeed, the MUSTN1 transcript codes for a protein involved in bone development and regeneration (Allison et al, 2006) and some alleles of the HLA-DPB1 gene have been associated with a relatively high risk of RA occurrence (Chen et al, 2005). The opposite variations in transcript levels seen in responders vs non-responders strongly suggest that the informative transcripts originated from TNFα-regulated genes. In fact, a TNFα-dependent expression of the CXCL5, CYP3A4, LAMR1, MCP, and PSMB9 genes, as noted here, was previously described (Gao et al, 1991; Koch et al, 1994; Persson et al, 2003; Chun et al, 2002; Clausse et al, 1998) However, only two of the present transcripts, namely MCP and PTPN12, are found among lists of genes that are directly regulated by the TNFα/NFkB pathway, whether in RA (Hyc et al, 2003) or in another context (Groettrup et al, 2001; Taberner et al, 2005). Therefore, it is likely that most of the transcripts are indirect TNFα targets.

Determination of Expression Level

Determination of the expression level of a gene can be performed by a variety of techniques. Generally, the expression level as determined is a relative expression level.

More preferably, the determination comprises contacting the sample with selective reagents such as probes, primers or ligands, and thereby detecting the presence, or measuring the amount, of polypeptide or nucleic acids of interest originally in the sample. Contacting may be performed in any suitable device, such as a plate, microtiter dish, test tube, well, glass, column, and so forth In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In a preferred embodiment, the expression level may be determined by determining the quantity of mRNA.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a preferred embodiment, the invention provides an in vitro method for predicting whether a patient would be responsive to a treatment with a TNFα blocking agent, which method comprises determining the expression level of eight genes in a biological sample of said patient, wherein said genes are EPS15, HLA-DPB1, AKAP9, RASGRP3, MTCBP-1, PTNP12, MRPL22 and RPS28, which method comprises the steps of providing total RNAs extracted from PBMCs obtained from a blood sample of the patient, and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, et 2006)

In this context, the invention further provides a DNA chip comprising a solid support which carries nucleic acids that are specific to EPS15, HLA-DPB1, AKAP9, RASGRP3, MTCBP-1, PTNP12, MRPL22 and RPS28 genes.

Another subject of the invention is such DNA chip, which further carries nucleic acids that are specific to any or all of the genes of Table B.

Other methods for determining the expression level of said genes include the determination of the quantity of proteins encoded by said genes.

Such methods comprise contacting a biological sample with a binding partner capable of selectively interacting with a marker protein present in the sample. The binding partner is generally an antibody, that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with an antibody against the protein to be tested. A biological sample containing or suspected of containing the marker protein is then added to the coated wells. After a period of incubation sufficient to allow the formation of antibody-antigen complexes, the plate (s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Therapeutic Applications

A method for treating a TNFα-related disease is contemplated, which method comprises
a) a preliminary step of testing whether a patient with a TNFα-related disease would be responsive to a treatment with a TNFα blocking agent, by determining the expression level of eight genes in a biological sample of said patient, wherein said genes are EPS15, HLA-DPB1, AKAP9, RASGRP3, MTCBP-1, PTNP12, MRPL22 and RPS28; hereby classifying the patient as responder or non responder;
b) a step of administering a TNFα blocking agent to a patient classified as responder.

The classification of the patient—as responder or non-responder—is made according to the combined expression level of said eight genes. It allows to define a subgroup of patients who will be responsive to a treatment with a TNFα blocking agent.

A further subject of the invention is then the use of a TNFα blocking agent, such as infliximab, for the preparation of a medicament for treating a patient with a TNFα-related disease, such as rheumatoid arthritis, which patient being classified as responder to a treatment with a TNFα blocking agent, by determining the expression level of said eight genes in a biological sample of said patient.

The example illustrates the invention without limiting its scope.

Example

Gene Profiling in White Blood Cells Predicts Infliximab Responsiveness in Rheumatoid Arthritis As indicators of responsiveness to TNFα blocking agent are lacking in rheumatoid arthritis, the inventors have used gene profiling in peripheral blood mononuclear cells to predict a good vs poor response to infliximab. Thirty three patients with an active disease (Disease Activity Score 28 >5.1) which resisted weekly metothrexate therapy were further given infliximab at baseline, weeks 2 and 6, and every 8th week. The patients were categorized as responders whenever a change of Disease Activity Score 28 $\geq$ 1.2 was obtained at 3 months. Mononuclear cell RNAs were collected at baseline and at 3 months from responders and non-responders. The baseline RNAs were hybridized to a microarray of ca. 10.000 non-redundant human cDNAs. In 6 responders and 7 non-responders, 41 mRNAs identified by microarray were expressed as a function of the response to treatment and an unsupervised hierarchical clustering perfectly separated these responders from non-responders. Informativeness of 20 of these 41 transcripts, as measured by qRT-PCR, were reassessed in 20 further patients. The combined levels of these 20 transcripts properly classified 16/20 patients in leave-one-out procedure, with a sensitivity of 90% and a specificity of 70%, whereas a set of only 8 transcripts properly classified 18/20 patients. Trends for changes in various transcript levels at 3 months tightly correlated with treatment responsiveness and a down-regulation of specific transcript levels was observed in non-responders only. The present gene profiling obtained by a non-invasive procedure will be used to predict the likely responders to an infliximab/methotrexate combination.

This study is described in greater details below.

Patients and Methods

Patients

A total of 33 patients, fulfilling the American College of Rheumatology (ACR) criteria for RA (Arnet F C. et al. 1987) and followed in Rouen University Hospital were included in this study. The criteria for patient eligibility were: methotrexate treatment; disease activity score 28 (DAS28)$\geq$5.1; resistance to at least one DMARD (methotrexate included). Exclusion criteria were: evolving infectious disease; age <18 years; no contraception; pregnancy; cancer less than 5 years old; cardiac failure (stage III-IV of the New York Heart Association); infliximab allergy. This protocol (numbered 2003/007) was approved by the ethics committee of Haute-Normandie (France) and all participants signed an informed consent at time of enrolment. For one month or more before the start of this study, every patient was given fixed amounts of DMARD and nonsteroidal anti-inflammatory drug (NSAID) and did not receive any intra-articular steroid injection. During this study, every patient was given the same doses of methotrexate and prednisone as used before, and was treated with infliximab (Remicade®, by Schering-Plough, France) as recommended by the manufacturer and the French Drug Agency AFSSAPS (i.v. 3 mg/kg infliximab at weeks 0, 2, 6, and every 8th week). Before each infliximab infusion, DAS28, plasma CRP level, patient's assessment of pain (0-100 mm visual analogue scale, VAS), duration of morning stiffness, and physical function scored with the french version of the Health Assessment Questionnaire (HAQ) for RA (Guillemin F. et al. 1991) were recorded. Just before the 4th infusion (i.e. at 3 months), the patients were categorized as responders whenever a change of DAS28 ≧1.2 was obtained. All others were categorized as non-responders.

PBMC Isolation and mRNA Extraction and Labelling

The PBMCs were isolated from venous blood by Ficoll-Hypaque centrifugation and total RNAs were extracted by a standard phenol/chloroform procedure, quality controlled on an Agilent 2100 Bioanalyzer (Agilent Technologies, Palo Alto, USA) and frozen at −800° C. until further used. An internal, arbitrary standard was made of a mixture of total RNAs from PBMCs taken from 3 healthy donors. The oligodT-primed poly(A) mRNAs were labelled with [α33P] dCTP as previously described (Coulouarn et al. 2004), and the resulting, labelled cDNAs were immediately used for hybridization.

Transcriptome Analysis and q-RT-PCR

The array that was used, covering 12,000 cDNA probes for 10,000 non-redundant genes and various negative controls, as well as nylon arraying of PCR-amplified probes and hybridization of [α33p]dCTP-labelled mRNAs have all been extensively described and validated in a previous report (Coulouarn et al. 2004). Briefly, cDNA probes selected on the basis of a tissue-preferred expression in liver corresponded to genes with a liver-restricted expression (10% of the probes) as well as genes with an hepatic expression along with a broad expression in some (50%) or many non-hepatic tissues (40%) (Coulouarn et al. 2004). All arrays were made from a single batch of cDNA probes. Every RNA sample was hybridized at least twice on separate arrays. Whenever necessary, the sequence of cDNA probes was controlled with an ABI3100 capillary sequencer (Applied Biosystems). Real-time, quantitative reverse transcription PCR (q-RT-PCR) of mRNAs and normalization with the 18S RNA amount were done in duplicate as described (Coulouarn et al. 2004) and the primers designed with the Primer3 software (Primer 3: found on the world wide web at frodo.wi.mit.edu) are listed in Table 1.

TABLE 1

Primers used for qRT-PCR.

| Transcript | Forward | SEQ ID NO | Reverse | SEQ ID NO |
| --- | --- | --- | --- | --- |
| AKAP9 | 5'-TGTTACTGGGTGGGTTCCAG-3' | 66 | 5'-CAGAACCTGTGACTCGATGC-3' | 67 |
| COX7AL2 | 5'-TGATTTCCCTGGAGGTTCTG-3' | 68 | 5'-CCCCGAGGTGACTAACTCAA-3 | 69 |
| ELMOD2 | 5'-AGCTCCTGCTCCCCCTAGTT-3' | 70 | 5'-TCGCTGCAATTCACACTTCC-3' | 71 |
| EPS15 | 5'-GTCTTCCTTCCCCTCCCTTG-3' | 72 | 5'-GCAGCATCAGAAGCCAACAC-3' | 73 |
| FBOX5 | 5'-CGCTGTAATTCACCTGCAAA-3' | 74 | 5'-GTACCAGGCAGGGGACCTAT-3' | 75 |
| HLA-DPB1 | 5'-GACCTTCCAGATCCTGGTGA-3' | 76 | 5'-CTTTCTTGCTCCTCCTGTGC-3' | 77 |
| LAMR1 | 5'-GCAGCAGGAACCCACTTAGG-3' | 78 | 5'-AATGGCAACAATTGCACGAG-3' | 79 |
| MCP | 5'-AGCAATTTGGAGCGGTAAGC-3' | 80 | 5'-GTCCAGGTGCAGGATCACAA-3' | 81 |
| MRLP22 | 5'-CTCCACAACTGCCTGGAGAA-3' | 82 | 5'-AACTGAGCCAAAGCCTGGTC-3' | 83 |
| MTCBP1 | 5'-GGAGAAGGGAGACATGGTGA-3' | 84 | 5'-ACGAGGCACGTGTTAGTTCC-3' | 85 |
| PFKFB4 | 5'-TGGATCCCAAGTCCTTTGTG-3' | 86 | 5'-CGCCTTGGACATCTCTTAGC-3' | 87 |
| PSMB9 | 5'-GGTTCTTGATTCCCGAGTGTC-3' | 88 | 5'-CAGCCAAAACAAGTGGAGGT-3' | 89 |
| PTPN12 | 5'-TCCAGCGGGAGGTATTCACT-3' | 90 | 5'-TGGTCCTTTGGGTTTTCCAC-3' | 91 |
| QIL1 | 5'-CCTCATCAAGGGAAGTGTGG-3' | 92 | 5'-GGAGTCACGGATGGGAAAGT-3' | 93 |
| RASGRP3 | 5'-CAGCAAAGGGCAGAAGTCAT-3' | 94 | 5'-TAATTGCCGTTGGAGGAGAC-3' | 95 |
| RPL35 | 5'-ACCTGAAGGTGGAGCTGTCC-3' | 96 | 5'-AGAACACGGGCAATGGATTT-3' | 97 |
| RPS16 | 5'-AGTTCTGCTTCTCGGCAGG-3' | 98 | 5'-TCTTGGAAGCCTCATCCACA-3' | 99 |
| RPS28 | 5'-GACCGGTTCTCAGGGACAGT-3' | 100 | 5'-TGACTCCAAAAGGGTGAGCA-3' | 101 |
| SCAM1 | 5'-TGTGGCCCAGTACACCTTCA-3' | 102 | 5'-CACGTAGCTGGCAGGGAATA-3' | 103 |
| TBL2 | 5'-GATGGGGCTACACCTTCAC-3' | 104 | 5'-TGACCCTTCAGGCTCCAGAT-3' | 105 |
| 18S | 5'-GTGGAGCGATTTGTCTGGTT-3' | 106 | 5'-CGCTGAGCCAGTCAGTGTAG-3' | 107 |

Image Analysis and Data Mining

Image analysis with the XDotsReader software, version 1.8 (COSE, Le Bourget, France), substractions of noise and spot background, and image normalization with the median value of all signals per image were done exactly as previously detailed (Coulouarn et al. 2004). A transcript was considered to be expressed if at least two hybridizations provided a positive signal. The resulting, normalized values were used for a selection of significantly regulated mRNAs, i.e. those with an abundance that differed in two or more comparisons between two samples, using a funnel-shaped confidence interval (p<0.05) calculated from every mRNA detected per hybridization (Coulouarn et al. 2004). This results in a false discovery rate (FDR) that is below 10% of the total number of regulated mRNAs. Statistical analyses were done with the R software. The TIGR Multiexperiment viewer (Tmev version 2.2) (TM4, microarray software suite, found on the world wide web at tm4.org) was used for i) unsupervised hierarchical clustering (HC) using the average dot product and complete linkage options, ii) leave-one-out cross-validation with the supervised learning classification tool Support Vector Machine (SVM) and iii) the supervised statistical tool Significance Analysis of Microarrays (SAM) for identification of discriminant transcripts (Tusher VG. et al. 2001) with an FDR set at <1%. Information about the clinical and experimental data complies with the recommendations for a Minimum Information About Microarray Experiments (MIAME) and the raw data have been deposited (accession number GSE3592) in the GEO repository (Gene Expression Omnibus: found on the world wide web at ncbi.nlm.nih.gov/projects/geo).

Results

RA Patients and Response to Treatment

Two sets of responders (R1 to 16) or non-responders (NR1 to 17) to an infliximab/methotrexate combination were so categorized at 3 months with the EULAR criteria, as recommended (Arnet FC. et al. 1988). Tables 2 and 0.3 provide demographic and clinical information of these 33 patients, at entry and at 3 months The average disease duration was 11-12 years, and the DAS28 score indicated that all these patients had a high level of RA activity, which fits with their resistance to one or more DMARDs. Before treatment all variables (but morning stiffness) including DAS28 were similar in responders vs non-responders and in subset 1 vs 2.

Following treatment, the DAS28 score significantly improved at 3 months in responders (average decrease: 2.3) whereas it remained high in non-responders (average decrease: 0.4). Within each set of responders or non-responders, the patients were randomly separated as a training subset (subset 1) for transcriptome analysis and a validation subset (subset 2) for qRT-PCR At this stage, the inventors paid attention to retaining a relatively large numbers of patients in subset 2. As noted in Tables 2 and 3, most features did not significantly differ between paired subsets 1 and 2.

TABLE 2

Demographic and clinical data of RA patients at entry of study.

| Parameter | Responders [a] | | Non-responders | |
|---|---|---|---|---|
| | subset 1 [b] (n = 6) | subset 2 (n = 10) | subset 1 (n = 7) | subset 2 (n = 10) |
| age (years) | 54.1 ± 13.8 [c] | 55.2 ± 9.2 | 56.1 ± 11.7 | 58.9 ± 11.6 |
| sex (men/women) | 1/5 | 2/8 | 1/6 | 4/6 |
| RA duration (years) | 11.7 ± 8 | 11.1 ± 7.3 | 12 ± 10.2 | 10.5 ± 5.3 |
| methotrexate (mg/week) [d] | 12.5 ± 5.5 | 13 ± 2.8 | 15.4 ± 2.7 [e] | 11.5 ± 3.2 |
| prednisone (mg/day) | 12.1 ± 5.6 | 8.5 ± 4.2 | 10.3 ± 8.7 | 8.2 ± 5.4 |
| patients with NSAIDs [f] | 3 | 6 | 5 | 4 |
| patients with rheumatoid factor | 4 | 8 | 5 | 6 |
| patients with anti-CCP abs [g] | 3 | 8 | 5 | 8 |

[a] categorized as indicated in Patients and Methods.
[b] transcript levels were measured by microarray in subsets 1 or qRT-PCR in subsets 2.
[c] mean ± SD.
[d] maximally tolerated dose in a given patient.
[e] significant difference between subsets 1 and 2 within non-responders (p < 0.05, Mann and Whitney's non parametric test).
[f] non-steroidal anti-inflammatory drugs.
[g] anti-cyclic citrullinated peptide antibodies.

TABLE 3

Clinical data at baseline and at 3 months.

| | Responders | | | | Non-responders | | | |
|---|---|---|---|---|---|---|---|---|
| | subset 1 | | subset 2 | | subset 1 | | subset 2 | |
| | baseline | 3 months [a] | baseline | 3 months | baseline | 3 months | baseline | 3 months |
| Morning stiffness (min) | 245 ± 126.4 [b] | 35 ± 24.5 * | 210 ± 81.2 | 58 ± 70.2 * | 179 ± 159.4 | 66.4 ± 86 * | 133.5 ± 84.4 ** | 62 ± 67.6 * |
| DAS28 [c] | 6.4 ± 1 | 4.2 ± 0.9 * | 6.2 ± 0.7 | 3.8 ± 0.6 * | 5.7 ± 0.8 | 5.3 ± 1 | 5.5 ± 1 | 4.9 ± 1 * |
| Pain (0-100 mm VAS) [d] | 59.3 ± 20.3 | 29.3 ± 9.3 * | 62.5 ± 15.5 | 31.3 ± 14.5 * | 69.3 ± 13.1 | 54.1 ± 22.1 | 60.9 ± 11.4 | 40.6 ± 18.4 * |
| ESR (mm/hour) [e] | 44 ± 26.2 | 27 ± 20.3 * | 27.2 ± 15.7 | 11.3 ± 5.2 * | 35.7 ± 25.7 | 28.3 ± 15.3 | 24.1 ± 11.5 | 27.8 ± 19.2 |

TABLE 3-continued

Clinical data at baseline and at 3 months.

| | Responders | | | | Non-responders | | | |
| --- | --- | --- | --- | --- | --- | --- | --- | --- |
| | subset 1 | | subset 2 | | subset 1 | | subset 2 | |
| | baseline | 3 months [a] | baseline | 3 months | baseline | 3 months | baseline | 3 months |
| CRP (mg/L) | 42 ± 29.8 | 20 ± 15.7 * | 28.6 ± 19.7 | 6.2 ± 6.1 * | 18.5 ± 12.7 | 13 ± 8.2 | 15.8 ± 15.6 | 11 ± 7.3 |
| HAQ score (0-3 scale) | 1.6 ± 0.4 | 0.9 ± 0.5 * | 1.8 ± 0.7 | 1.2 ± 0.7 * | 1.6 ± 0.4 | 1.2 ± 0.3 | 1.5 ± 0.4 | 1.5 ± 0.4 |

[a] i.e. response assessed just before the 4th infliximab/methotrexate infusion.
[b] mean ± SD. Significant differences between groups are noted as follows:
* difference at baseline vs 3 months in this subset ($p < 0.05$, paired Wilcoxon's test);
** difference between responders vs non-responders at baseline ($p < 0.05$, Mann and Whitney's test). All other comparisons were non-significant:
[c] disease activity score.
[d] patient's assessment of pain.
[e] ESR: erythrocyte sedimentation rate; CRP: C-reactive protein; HAQ: health assessment questionnaire.

Gene Profiling in Pre-Treatment PBMCs Correlates with Treatment Responsiveness

Gene profiling in PBMCs was studied in the two training subsets 1 from responders and non-responders (total, 13 patients). On average, 5282±1253 transcripts were detected in PBMCs, with 86% overlap in transcript identities between responders and non-responders (not detailed). To precisely identify the transcripts that were differentially regulated in responders vs non-responders, the inventors first selected every transcript whose level in at least one responder (non-responder) was significantly different from the median value in non-responders (responders). This was assessed with a funnel-shaped confidence interval (see Methods; p<0.05) and resulted in 2239 transcripts with an abnormal level in at least 1 out of these 13 patients. From these 2239 transcripts, the inventors next selected every transcript whose variation between responders and non-responders was statistically significant by t test (25 transcripts) and/or SAM (37 transcripts). These transcripts are detailed in Table 4 (total, 41 transcripts; overlap between t test and SAM selections, 21 transcripts). The identity of the corresponding microarray cDNA probes was verified by sequencing. Finally, the inventors performed an unsupervised hierarchical clustering of the 13 patients above (subsets 1). This was based on the levels of the or 37 transcripts indicated above, which in both instances resulted in a perfect separation of the responders and non-responders into two major clusters.

TABLE 4

Transcripts as predictors of infliximab responsiveness

| IMAGE clone [a] | encoded protein | symbol [b] | gene localiz. | SAM [c] | t test [d] |
| --- | --- | --- | --- | --- | --- |
| 295669 | Clone 10PTELO13 | — | — | −3.77 | 0.001 |
| 77684 | Cytochrome P450, family 3, subfamily A, polypeptide 4 | CYP3A4 | 7q21.1 | −2.90 | <10⁻⁴ |
| 417137 | A kinase (PRKA) anchor protein (yotiao) 9 | AKAP9 | 7q21-q22 | −2.83 | 0.002 |
| 415079 | Hypothetical protein DKFZp566M1046 | — | — | −2.78 | 0.001 |
| 1848509 | RP1 containing part of the thyroid hormone receptor-associated protein 3 | THRAP3 | 1p34.3 | −2.56 | ns |
| 234261 | RP11-750K11 | — | — | −2.53 | ns |
| 198699 | Chemokine (C-X-C motif) ligand 5 (ENA78) | CXCL5 | 4q12-q13 | −2.50 | ns |
| 730048 | Ribosomal protein SA (37LRP) | LAMR1 | 3p21.3 | −2.43 | 0.007 |
| 56923 | F-box protein 5 | FBXO5 | 6q25-q26 | −2.42 | 0.006 |
| 1524020 | RAS guanyl releasing protein 3 (calcium and DAG-regulated) | RASGRP3 | 2p25.1-p24.1 | −2.41 | 0.004 |
| 756784 | WD repeat domain 39 | WDR39 | 2q11.2 | −2.40 | ns |
| 244313 | Bac clone RP11-576F1 | — | — | −2.39 | 0.002 |
| 124452 | 6-phosphofructo-2-kinase/fructose-2,6-biphosphatase 4 | PFKFB4 | 3p22-p21 | −2.33 | 0.003 |
| 724887 | Major histocompatibility complex, class II, DP beta 1 | HLA-DPB1 | 6p21.3 | −2.32 | <10⁻⁴ |
| 416493 | Ribosomal protein L35 | RPL35 | 9q34.1 | −2.25 | ns |
| 191599 | Hypothetical protein FLJ13614 | — | — | −2.23 | 0.006 |
| 726045 | Ribosomal protein S16 | RPS16 | 19q13.1 | −2.24 | ns |
| 772993 | Similar to 40S ribosomal protein S28 | RPS28 | 19p13.2 | −2.23 | ns |
| 110169 | Proteasome subunit, beta type, 9 (LMP2) | PSMB9 | 6p21.3 | −2.17 | 0.006 |
| 346678 | Musculoskeletal, embryonic nuclear protein 1 | MUSTN1 | 3p21.1 | −2.16 | ns |
| 741027 | Vinexin beta (SH3-containing adaptor molecule-1) | SCAM-1 | 8p21.3 | −2.15 | ns |
| 428222 | Epidermal growth factor receptor pathway substrate 15 | EPS15 | 1p32 | −2.12 | 0.003 |
| 740374 | Transducin (beta)-like 2 | TBL2 | 7q11.23 | −2.12 | ns |
| 774502 | Protein tyrosine phosphatase, non-receptor type 12 | PTPN12 | 7q11.23 | −2.09 | ns |
| 320298 | Membrane-type 1 matrix metalloproteinase cytoplasmic tail binding protein-1 | MTCBP-1 | 2p25.2 | −2.04 | 0.005 |
| 148134 | RP1-29K1 containing the gene for KiAA0426 | — | — | ns | 0.002 |
| 127203 | Cytochrome P450, family 4, subfamily F, polypeptide 12 | CYP4F12 | 19p13.1 | ns | 0.005 |
| 428560 | QIL1 protein | QIL1 | 19p13.3 | ns | 0.009 |
| 810626 | Cytochrome c oxidase subunit VIIa polypeptide 2 like | COX7A2L | 2p21 | ns | 0.007 |
| 123983 | Clone PR13 | — | — | +1.80 | ns |
| 486624 | ELMO domain containing 2 | ELMOD2 | 4q31.21 | +1.85 | ns |
| 114519 | FLJ 14775 | — | — | +1.90 | 0.007 |
| 357960 | Mitochondrial ribosomal protein L22 | MRPL22 | 5q33.1-q33.3 | +1.99 | 0.009 |
| 82303 | Hypothetical protein BC009264 | — | — | +2.12 | ns |
| 247517 | Mucin and cadherin-like | MUCDHL | 11p15.5 | +2.40 | ns |

TABLE 4-continued

Transcripts as predictors of infliximab responsiveness

| IMAGE clone [a] | encoded protein | symbol [b] | gene localiz. | SAM [c] | t test [d] |
|---|---|---|---|---|---|
| 194455 | Membrane cofactor protein (CD46) | MCP | 1q32 | +2.30 | 0.005 |
| 247176 | RP116103J18 | — | — | +2.41 | $<10^{-4}$ |
| 195723 | Kininogen 1 | KNG1 | 3q27 | +2.46 | 0.009 |
| 239932 | ELAC homolog 2 | — | — | +2.46 | ns |
| 244896 | Aminoadipate aminotransferase | AADAT | 4q33 | +2.52 | 0.002 |
| 193472 | RP11-722P15 | — | — | +2.68 | 0.002 |

[a] IMAGE clone number as a unique identifier.
[b] bold characters indicate a transcript that was further tested by qRT-PCR.
[c] SAM value as an indicator of significant transcript variation in responders vs non-responders (ns, non significant). A positive or negative value indicates an over- or underexpression at baseline in responders vs non-responders, respectively.
[d] p value of a t test as an indicator of significant transcript variation in responders vs non-responders (ns, non significant).

With the PBMCs from further patients, the inventors wished to confirm that a combination of the above transcript levels could be used as a predictor of responsiveness. For this purpose, they aimed at measuring the levels of the 41 transcripts above by qRT-PCR and comparing them between the two validation subsets 2 (responders or non-responders, total 20 patients). However, among these 41 transcripts, 12 putative transcripts were merely identified by one IMAGE clone without knowledge of the intron/exon structure and hence they were not retained in this approach. Moreover, among the 29 remaining transcripts, 9 of them failed to provide reliable data by qRT-PCR, despite repeated attempts with various primers. Eventually, 20 out of their 41 transcripts could be reliably quantified by qRT-PCR: These 20 transcripts are those in bold characters in Table 4.

An unsupervised hierarchical clustering of the 20 patients in subsets 2, as based upon these 20 transcript levels, resulted in two major clusters of responders vs non-responders, with 5 (24%) misclassified patients (NR8, NR12, NR17, R13, R16). Despite its informativeness, such hierarchical clustering lacks statistical power, and hence the efficiency of the above set of 20 transcripts for patient classification was further evaluated in leave-one-out cross-validation (TM4, microarray software suite: found on the world wide web at tm4.org). This procedure identified 4 misclassified patients and indicated that this set of transcripts provides 90% sensitivity and 70% specificity for identification of responders and non-responders (Table 5).

TABLE 5

Performances of the number of selected transcripts for prediction of responsiveness

| Number of selected transcripts [a] | 20 transcripts | 8 transcripts |
|---|---|---|
| Number of NR patients classified as NR [b] | 7 | 10 |
| Number of NR patients classified as R [b] | 3 | 0 |
| Number of R patients classified as R [b] | 9 | 8 |
| Number of R patients classified as NR [b] | 1 | 2 |
| Fisher's exact test | p < 0.02 | p < 0.0007 |
| Sensitivity | 90% | 80% |
| Specificity | 70% | 100% |
| Positive predictive value | 75% | 100% |
| Negative predictive value | 87.5% | 83% |

[a] in bold characters in Table 4;
[b] by leave-one-out cross-validation with 20 patients including 10 non-responders (NR) and 10 responders (R) (referred to as validation subsets 2)

To determine the minimal number of transcripts that should be measured for an acceptable prediction of responsiveness, the inventors tested in the 20 patients from the subsets 2 above a series of combinations of transcripts, and they varied the number and identity of the transcripts actually used (not detailed). With a given set of only 8 transcripts, 16 out of 20 patients could be correctly classified as responders or non-responders by hierarchical clustering. Finally, leave-one-out cross-validation (Table 5) identified only 2 misclassified patients and indicated that a given set of 8 transcripts as a predictor of responsiveness was at least as accurate as the set of 20 transcripts above.

Post-Treatment Transcript Levels Correlate with Treatment Responsiveness

The inventors investigated whether the differences in transcript levels as seen in responders vs non-responders at baseline were also retained at 3 months. The data obtained in PBMCs by qRT-PCR are presented in FIG. 1. In responders, 18 out of 20 transcripts (90%) exhibited a trend towards an increased level at 3 months, although the differences with respect to the levels at baseline were not significant. Strikingly, in non-responders 19 out of 20 transcripts (95%) exhibited an opposite trend, i.e. a decreased level at 3 months, and this difference was statistically significant for each of 8 transcripts (FIG. 1). Overall, the differences in numbers of up- vs down-regulated transcripts in responders vs non-responders were highly significant, whether considering only the number of transcripts with a significant difference at baseline vs 3 months (n=8, p=$3.10^{-3}$, Fisher's exact test) or considering the complete set of transcripts and associated trends (n=20; p<$10^{-4}$ by Fisher's exact test, or p=0.007 by analysis of variance). This argued for a regulation of the corresponding genes by one (or more) TNFα-dependent pathway(s).

Discussion

The small set of biological markers usually used for RA diagnosis or prognosis is unable to predict individual responsiveness to TBA (Lequerré T. et al. 2005). Therefore, for the sake of such a prediction, global approaches based on proteomics or transcriptomics have been recently considered (Dryna S. et al. 2004; Jarvis J N. 2005). However, in the RA context, proteomic analysis is still under development (Dryna S. et al. 2004). Moreover, very few informative transcripts have been identified by gene profiling (Kekow J. et al. 2004) and the few studies that used this approach have relied on the differences in transcript levels measured at baseline vs 2-3 days after treatment onset (Meisel C. et al. 2004). This required exposure of every patient to treatment. Furthermore, the narrow time frame of this procedure may blur some significant but late variations with respect to baseline, which eventually limits transcript informativeness. In contrast, the inventors have now measured transcript levels at baseline as the single predictor of responsiveness. In clinical practice prediction can then be done without any exposure to treatment, which allows the latter to be restricted to responders.

Three months of treatment was chosen as the endpoint of this study, as recently recommended by international experts (Allison D B. 2006), because the objective of an efficient RA treatment is a rapid response. Would this early evaluation at 3 months disclose a moderate or absent response, this procedure allows another treatment to be used as early as possible. Also, using the DAS28 evolution at three months for classifying the 33 patients as responders or on-responders turned out to be quite reliable in the long run. Indeed, 22 out of 33 patients could be followed for three more years and their infliximab responsiveness, or lack thereof, did not vary over this period, even when increasing infliximab amount and frequency in non-responders (non-detailed).

The inventors aimed at identifying a list of transcripts whose combined levels could be related to infliximab/methotrexate responsiveness. The mixture of a cytokine inhibitor (infliximab) and an inhibitor of cell proliferation (methotrexate) is likely to regulate or even co-regulate a complex set of genes and hence this is a limitation if an understanding of some underlying events in RA is desired. Gene expression was measured in PBMCs, because this is an acknowledged, non-invasive procedure for diagnosis or prognosis of autoimmune diseases (Olsen N J. 2004). Specifically, in a RA context, PBMCs as a surrogate tissue are advantageous as they allow for a screening in any subject, whereas synovium is amenable to analysis in a few patients. However, a drawback of such a PBMC analysis is the lack of a clear-cut relationship between PBMCs and the affected synovium, which prevents the resulting data from providing an understanding of the RA-associated events in joints. Also, they have analyzed the PBMC transcriptome with an arbitrary collection of ca. 10,000 cDNA probes (Coulouarn C et al. 2004). Since this restrictive procedure cannot measure every transcript expressed in the PBMCs, it does not intend to provide a genome-wide view of the RA-associated gene dysregulations in this tissue. Yet, this approach is quite acceptable when inferring prognosis from gene profiling is the major task. Overall, the present study was not primarily designed to increase our understanding of RA physiopathology but it was mostly suited to a predictive usage of some combined transcript levels. Eventually, the present data illustrate that a non-invasive transcriptome analysis done in PBMCs with an array of probes devoid of a specific selection towards the disease under study enables an efficient prediction of treatment responsiveness.

By t test and/or SAM, the inventors have identified a short list of 25-37 transcripts whose combined expression levels in PBMCs are an efficient discriminator of responders vs non-responders to infliximab/methotrexate. Many of the 25 transcripts identified by t test were no longer significant when using Bonferroni's correction to adjust statistics for the multiple transcripts analyzed, but Bonferroni's correction has been recognized as a drastic one when used in this context, which contrasts with the SAM-associated FDR (Allison D B. et al. 2006). Moreover, t test and SAM cross-validated each other for most of the 20 transcripts eventually selected for qRT-PCR as 13/20 (65%) such transcripts were significant with both tests (Table 4). Measuring these 20 transcript levels by qRT-PCR indicated that their performance as a predictor of responsiveness was equal to that obtained with 37 transcripts. Ultimately, a given combination of 8 selected transcripts (75% of them being significant with t test and SAM) as a predictor of responsiveness was as powerful as any higher number of transcripts. This observation that a given combination of very few transcripts can equal or even outperform the predictive strength of a higher number of transcripts has also been reported in another context, namely the response to hepatitis C treatment (Chen L. et al. 2005). This small size for an informative gene set is most encouraging when the need comes for the development of a reliable, fast and cheap assay for measures of informative transcript levels in a clinical setting.

Abbreviations: ACR, American College of Rheumatology; CRP, C-reactive protein; DAS, disease activity score; DMARD, disease-modifying anti-rheumatic drug; EULAR, EUropean Ligue Against Rheumatism; ESR, erythrocyte sedimentation rate; FDR, false discovery rate; HAQ, health assessment questionnaire; MIAME, minimum information about microarray experiments; NR, non responder; PBMC, peripheral blood mononuclear cell; q-RT-PCR, real-time, quantitative reverse transcriptase PCR; R, responder; RA, rhumatoid arthritis; SAM, significance analysis of microarrays; SVM, support vector machine; TBA, TNFa blocking agent; TNFa, tumor necrosis factor-a; VAS, visual analogue scale

REFERENCES

Allison D B, Cui X, Page G P, Sabripour M: Microarray data analysis: from disarray to consolidation and consensus. Nat Rev Genet 2006, 7:55-65.

Arnett F C, Edworthy S M, Bloch D A, McShane D J, Fries J F, Cooper N S, Healey L A, Kaplan S R, Liang M H, Luthra H S, et al. The American Rheumatism Association 1987 revised criteria for the classification of rheumatoid arthritis. Arthritis Rheum 1988, 31:315-324.

Bridges S L Jr: Genetic markers of treatment response in rheumatoid arthritis. Arthritis Rheum 2004, 50:1019-1022.

Chen L, Borozan I, Feld J, Sun J, Tannis L L, Coltescu C, Heathcote J, Edwards A M, McGilvray I D: Hepatic gene expression discriminates responders and nonresponders in treatment of chronic hepatitis C viral infection. Gastroenterology 2005, 128:1437-1444.

Chun Y J, Lee S, Yang S A, Park S, Kim M Y: Modulation of CYP3A4 expression by ceramide in human colon carcinoma HT-29 cells. Biochem Biophys Res Commun 2002, 298:687-692.

Clausse N, van den Brule F, Delvenne P, Jacobs N, Franzen-Detrooz E, Jackers P, Castronovo V: TNF-alpha and IFN-gamma down-regulate the expression of the metastasis-associated bifunctional 37LRP/p40 gene and protein in transformed keratinocytes. Biochem Biophys Res Commun 1998, 251:564-569.

Coulouarn C, Lefebvre G, Derambure C, Lequerré T, Scotte M, François A, Cellier D, Daveau M, Salier J P: Altered gene expression in acute systemic inflammation detected by complete coverage of the human liver transcriptome. Hepatology 2004, 39:353-364.

Cuchacovich M, Ferreira L, Aliste M, Soto L, Cuenca J, Cruzat A, Gatica H, Schiattino I, Perez C, Aguirre A, Salazar-Onfray F, Aguillon J C: Tumour necrosis factor-alpha (TNF-alpha) levels and influence of −308 TNF-alpha promoter polymorphism on the responsiveness to infliximab in patients with rheumatoid arthritis. Scand J Rheumatol 2004, 33:228-232.

Drynda S, Ringel B, Kekow M, Kuhne C, Drynda A, Glocker M O, Thiesen H J, Kekow J: Proteome analysis reveals disease-associated marker proteins to differentiate RA patients from other inflammatory joint diseases with the potential to monitor anti-TNFalpha therapy. Pathol Res Prac 2004, 200:165-171.

Gao X, Fernandez-Vina M, Olsen N J, Pincus T, Stastny P: HLA-DPB1*0301 is a major risk factor for rheumatoid factor-negative adult rheumatoid arthritis. Arthritis Rheum 1991, 34:1310-1312.

Groettrup M, van den Broek M, Schwarz K, Macagno A, Khan S, de Giuli R, Schmidtke G: Structural plasticity of the proteasome and its function in antigen processing. Crit Rev Immunol 2001, 21:339-358.

Guillemin F, Braincon S, Pourel J: Measurement of the functional capacity in rheumatoid polyarthritis: a French adaptation of the Health Assessment Questionnaire (HAQ). Rev Rhum Mal Osteoartic. 1991, 58:459 A65.

Hoheisel, Nature Reviews, Genetics, 2006, 7:200-210

Hyc A, Osiecka-lwan A, Strzelczyk P, Moskalewski S: Effect of IL-1 beta, TNF-alpha and IL-4 on complement regulatory protein mRNA expression in human articular chondrocytes. Int J Mol Med 2003, 11:91-94.

Jarvis J N, Centola M: Gene-expression profiling: time for clinical application? Lancet 2005, 365:199-200.

Kang C P, Lee K W, Yoo D H, Kang C, Bae S C: The influence of a polymorphism at position −857 of the tumour necrosis factor alpha gene on clinical response to etanercept therapy in rheumatoid arthritis. Rheumatology 2005, 44:547-552.

Kekow J, Koczan D, Drynda S, Drynda A, Guthke R, Thiesen H J. Early identification of responders to anti-TNFα therapy by microarrays technique [abstract]. Arthritis Rheum 2004, Suppl 50:117.

Koch A E, Kunkel S L, Harlow L A, Mazarakis D D, Haines G K, Burdick M D, Pope R M, Walz A, Strieter R M: Epithelial neutrophil activating peptide-78: a novel chemotactic cytokine for neutrophils in arthritis. J Clin Invest 1994, 94:1012-1018.

Lequerré T, Viftecoq O, Le Loët X: Comment about the editorial by Benedicte Mugnier and Jean Roudier entitled "Factors predicting responsiveness to anti-TNFa therapy in patients with rheumatoid arthritis: using biotherapies rationally". Joint Bone Spine 2005, 72:346-347.

Meisel C, Newton J L, Harney S M, Wordsworth B P, Brown M A: Gene expression profiling of treatment response to anti-TNF-alpha therapy in rheumatoid arthritis [abstract]. Arthritis Rheum 2004, Suppl 50:120.

Mugnier B, Balandraud N, Darque A, Roudier C, Roudier J, Reviron D: Polymorphism at position −308 of the tumor necrosis factor alpha gene influences outcome of infliximab therapy in rheumatoid arthritis. Arthritis Rheum 2003, 48:1849-1852.

Mugnier B, Roudier J: Factors predicting responsiveness to anti-TNFα therapy in patients with rheumatoid arthritis: using biotherapies rationally. Joint Bone Spine 2004, 71:91-94.

Persson T, Monsef N, Andersson P, Bjartell A, Malm J, Calafat J, Egesten A: Expression of the neutrophil-activating CXC chemokine ENA-78/CXCL5 by human eosinophils. Clin Exp Allergy 2003, 33:531-537.

Olsen N J, Moore J H, Aune T M: Gene expression signatures for autoimmune disease in peripheral blood mononuclear cells. Arthritis Res Ther 2004, 6:120-128.

Taberner M, Scott K F, Weininger L, Mackay C R, Rolph M S: Overlapping gene expression profiles in rheumatoid fibroblast-like synoviocytes induced by the proinflammatory cytokines interleukin-1 beta and tumor necrosis factor. Inflamm Res 2005, 54:10-16.

Tusher V G, R Tibshirani, Chu G: Significance analysis of microarrays applied to the ionizing radiation response. Proc Nat Acad Sci USA 2001, 98:5116-5121.

Van Gestel A M, Prevoo M L L, van't H of M A, et al. Development and validation of the European League Against Rheumatism response criteria for rheumatoid arthritis. Arthritis Rheum 1996; 39:34-40

The invention claimed is:

1. An in vitro method for predicting whether a patient would be responsive to a treatment with a TNFα blocking agent, which method comprises determining the expression level of eight genes in a biological sample of said patient, wherein said genes are EPS15, HLA-DPB1, AKAP9, RASGRP3, MTCBP-1, PTNP12, MRPL22 and RPS28.

2. The method of claim 1, wherein the patient is with rheumatoid arthritis.

3. The method of claim 2, wherein the TNFα blocking agent is an anti-TNFα antibody.

4. The method of claim 2, wherein the patient is with rheumatoid arthritis that is active.

5. The method of claim 3, wherein the TNFα blocking agent is an anti-TNFα antibody.

6. The method of claim 1, wherein the TNFα blocking agent is an anti-TNFα antibody.

7. The method of claim 6, wherein the antibody is infliximab.

8. The method of claim 1, further comprising the step of comparing the combined expression level of said genes with reference values obtained from responder and non-responder groups of patients.

9. The method of claim 1, wherein the patient receives a first-line therapy other than TNFα blocking agent.

10. The method of claim 9, wherein the patient is treated with methotrexate, azathoprine or leflunomide.

11. The method of claim 1, wherein the biological sample is blood.

12. The method of claim 1, wherein the expression level is determined by quantifying the level of mRNA of said genes in the biological sample.

13. The method of claim 12, which comprises the steps of providing total RNAs extracted from PBMCs obtained from a blood sample of the patient, and subjecting the RNAs to amplification and hybridization to specific probes.

14. The method of claim 12, wherein the expression level is determined by real-time quantitative or semi-quantitative RT-PCR.

15. The method of claim 12, wherein the expression level is determined by using a DNA chip.

16. The method of claim 1, further comprising determining the expression level of one or more genes selected from the group consisting of AADAT, COX7AL2, CXCL5, ELMOD2, FBXO5, KNG1, LAMR1, MUCDHL, PFKFB4, PSMB9, RPL35, RPS16, TBL2, THRAP3, 193472 Kininogen 1, 239932, QIL-1, SCAM-1, MUSTN1, WDR39, 114519, 415079, 244313, 295669, 234261, 123983, 82303, and 247176.

17. A DNA chip comprising a solid support which carries nucleic acids that hybridize under a stringent condition to the EPS15, HLA-DPB1, AKAP9, RASGRP3, MTCBP-1, PTNP12, MRPL22, and RPS28 genes.

18. The chip of claim 17, which further carries nucleic acids that hybridize under a stringent condition to any or all of the genes selected from the group consisting of AADAT, COX7AL2, CXCL5, ELMOD2, FBXO5, KNG1, LAMR1, MUCDHL, PFKFB4, PSMB9, RPL35, RPS16, TBL2, THRAP3, 193472 Kininogen 1, 239932, OIL-1, SCAM-1, MUSTN1, WDR39, 114519, 415079, 244313, 295669, 234261, 123983, 82303, and 247176.

19. A method for treating a patient suffering from a TNFα-related disease, the method comprising:
identifying a patient who suffers from a TNFα-related disease and is classified as a responder to TNFα blocking agents, wherein classification as a responder is effected by determining expression levels in the patient of the EPS15, HLA-DPB1, AKAP9, RASGRP3, MTCBP-1, PTNP12, MRPL22 and RPS28 genes, and comparing the combined expression level of said genes with pre-determined reference values obtained from responder and non-responder groups; and
administering to the patient an effective amount of a TNFα blocking agent.

20. The method of claim 19, wherein the TNFα blocking agent is infliximab.

21. The method of claim 19, wherein the disease is rheumatoid arthritis.

* * * * *